United States Patent [19]
Schmidt et al.

[11] Patent Number: 5,861,153
[45] Date of Patent: Jan. 19, 1999

[54] SKIN EQUIVALENT COMPRISING LANGERHANS' CELLS

[75] Inventors: Rainer Schmidt; Marcelle Regnier, both of Paris; Daniel Schmitt, Heyrieux; Marie-Jeanne Staquet, Decines, all of France

[73] Assignee: Société L'Oréal S.A., Paris, France

[21] Appl. No.: 785,287

[22] Filed: Jan. 23, 1997

[30] Foreign Application Priority Data

Jan. 23, 1996 [FR] France .................................. 96 00743

[51] Int. Cl.$^6$ .............................. C12N 5/08; C12N 5/06
[52] U.S. Cl. .......................................................... 424/93.7
[58] Field of Search .............................................. 424/93.7

[56] References Cited

FOREIGN PATENT DOCUMENTS

| 0470681 | 2/1992 | European Pat. Off. . |
| 90/02796 | 3/1990 | WIPO . |

OTHER PUBLICATIONS

Prignano et al., Molecular Biology of the Cell 7 (SUPPLE.) 142A 1996.
Koch et al., J Exp Med 171(1): 159–172 (1990).
Witmer–Pack et al., J Exp Med 166(5): 1484–1498 (1987).
Heufler et al., J Exp Med 167(2): 700–705 (1988).
Czernielewski et al., Arch Dermatol Res 276(5): 288–292 (1984).

*Primary Examiner*—Jean C. Witz
*Attorney, Agent, or Firm*—Burns, Doane, Swecker & Mathis, L.L.P.

[57] ABSTRACT

The present invention relates to a reconstructed skin model, characterized in that it comprises an epidermis equivalent on a support, the said epidermis equivalent comprising at least keratinocytes and at least induced or noninduced precursors of Langerhans' cells, as well as the process for preparing the said skin equivalent.

The invention also relates to an epidermis equivalent, characterized in that it comprises at least keratinocytes and at least induced or noninduced precursors of Langerhans' cells and to the process for preparing it.

36 Claims, No Drawings

SKIN EQUIVALENT COMPRISING LANGERHANS' CELLS

The present invention relates to a new skin equivalent, to the process for producing it, to the epidermis equivalent contained in this skin equivalent and to the process for preparing it.

Attempts have been made for several years to develop reconstructed skin models which make it possible to carry out the studies necessary for the greatest understanding of the role of the skin both in the mechanical domain and in the physiological domain.

Thus, it has been possible to develop models similar to the human skin to a greater or lesser degree. There may be mentioned for example the models described in patents or in patent applications EP 285471, EP 285474, EP 418035, WO-A-90 02796, WO-A-9116010, EP 197090, EP 20753, FR 2665175, FR 2689904.

Most generally, the reconstructed skin models described in these documents consist of human keratinocytes deposited on a support, often a dermis equivalent, and cultivated under conditions such that they enter into a programme of differentiation leading to the formation of an epidermis equivalent.

However, the natural human epidermis consists mainly of three types of cells which are the keratinocytes, the most predominant, the melanocytes and the Langerhans' cells. Each of these cell types contributes through its own functions to the essential role played in the body by the skin. The Langerhans' cells are involved in the skin's immune defences. It has long been known that these cells occupy an essential place in the host's immune defences, in particular as first barrier against external aggression.

The Langerhans' cells are cells derived from the bone marrow which can be characterized by the presence of Birbeck granules and the expression of the CD1a antigenic marker (CD1a-positive cells) (Rowden et al., Nature 268: 247–248, 1977). They play a key role in the initiation of the immune responses directed against the antigens introduced into the skin or newly generated by it. When placed in contact with an allergen, the Langerhans' cells migrate towards the ganglia where they trigger T cell specific reactions. In this regard, they are therefore assimilated to antigen-presenting cells which are essential for correct functioning of the T lymphocytes.

Thus, the main function of the Langerhans' cells is to provide a sensitive signal in the skin's immune response induced against a wide variety of antigens including contact allergens, tumoral antigens and microorganisms.

It can therefore be concluded that these cells are probably involved in a large number of skin pathologies.

The document WO-A-90 02796 suggests adding Langerhans' cells isolated from fresh skin samples to cultures of keratinocytes and melanocytes in a three-dimensional system of skin culture. This same document specifies that the growth in culture of such cells is difficult. It is in fact the case that Langerhans' cells purified from a skin sample are cells derived from precursors which have progressed in their differentiation cycle to the point of becoming CD1a-positive cells and that these isolated cells no longer progress in their differentiation cycle.

The in vitro culture of such cells amounts to maintaining in a state of survival because of the incapacity of these cells to multiply. Indeed, these cells stop and die without having fulfilled their role. The same is true when these cells are introduced into a reconstructed skin model. Thus, even if it is suggested to introduce Langerhans' cells in this document, the reconstructed skin obtained could not be satisfactory since the Langerhans' cells do not survive.

The melanocytes are localized in the basal layer of the epidermis. They are the site of melanogenesis and because of their close contact with the keratinocytes, they transfer to them the neosynthesized melanin in the form of melanosomes, thus giving the skin its colour. The type and quantity of melanin contained in the melanosomes determines the colour of the skin. Furthermore, the melanin mainly constitutes an effective barrier for protection against solar radiation and in particular ultraviolet radiation. A reconstructed skin model which has incorporated melanocytes is described in patent application WO-A-9351165.

It can therefore be understood that the reconstructed skin models described in the prior art only allow incomplete studies of the role and/or of the reactions of the skin. Indeed, the absence of Langerhans' cells, cells which are essential for the skin's immune defences, in these models make them unusable for immunological studies in vitro. Moreover, it can be assumed that the pharmacological and/or toxicological studies carried out with these models have been able to reflect only part of the reality of the interactions because of the absence of this essential component of the skin which the Langerhans' cells constitute.

Independently of the natural phenomena which lead to the symptoms linked to the so-called sensitive and/or allergic skins, phenomena which such a model will make it possible to better understand, industry in general, and the cosmetic industry in particular, is increasingly introducing new compounds into its compositions. One of the major problems it is faced with is then the evaluation of the harmful effects that these compounds might induce in contact with the skin, in particular in terms of contact sensitization.

For ethical reasons, it is obvious that this evaluation cannot be performed on man or on animals.

The value of an in vitro model can thus be understood which can allow, by grasping the skin's defence mechanisms, a better understanding of the symptoms linked to the so-called sensitive and/or allergic skins and an evaluation of the harmful effects of compounds which can be potentially used in industry.

The applicant, who for many years has been interested in the field of reconstructed skins, has now discovered that it is possible to incorporate at least precursors of Langerhans' cells, induced beforehand or otherwise, into a reconstructed skin model.

The subject of the present invention is therefore a reconstructed skin model, characterized in that it comprises an epidermis equivalent on a support, the said epidermis equivalent comprising at least keratinocytes and at least induced or noninduced precursors of Langerhans' cells.

The expression "induced precursors of Langerhans' cells" covers, in this text, any cell, normal or pathological, which has undergone, prior to it being placed in co-culture, at least one treatment intended to confer on it the characteristics of a Langerhans' cell, that is to say a CD1a-positive cell, without prejudging the acquisition or otherwise of the CD1a-positive character by this cell.

In normal skin, the Langerhans' cells are located in the suprabasal part of the epidermis.

Preferably, the reconstructed skin model according to the invention has at least induced or noninduced precursors of Langerhans' cells located in the suprabasal part of the epidermis equivalent.

It is clearly understood that the skin equivalent of the invention may comprise any other cell type which could be incorporated into it.

The applicant has succeeded in establishing a process for preparing a skin equivalent comprising an epidermis equivalent on a support, the said epidermis equivalent comprising at least keratinocytes and at least induced or noninduced precursors of Langerhans' cells.

The subject of the invention is also a process for the preparation of a skin equivalent as described above, characterized in that keratinocytes and at least induced or noninduced precursors of Langerhans' cells are co-cultivated on the support.

For ease of understanding, the use of the term "co-culture" (or of related terms) should be understood as referring to the cell cultures carried out on the support allowing the formation of the reconstructed skin, without necessarily implying the presence of more than one cell species. The terms "culture" and "cultivate" are understood in this case as relating to cell cultures carried out in a conventional manner, for example in traditional cell culture dishes.

The support used according to the invention may be any one of those described in the prior art. By way of example, there may be mentioned, as support, mixed collagen/fibroblast lattices, the dermis previously freed of the epidermis, artificial membranes such as, for example, filters of the Millipore trade mark, collagen-based subcutaneous substitutes, plastic or any other support compatible with cell viability.

Preferably, the support consists of a dermis previously freed of the epidermis.

Whatever the support chosen, the procedure for its use according to the invention may be any of the procedures described in the prior art.

Preferably, according to the invention, when the support consists of a dermis previously freed of the epidermis, the procedure described in Prunieras et al., Ann. Chir. Plast., 1979, 24, No.4, 357–362 is used.

According to the invention, to obtain the epidermis equivalent comprising at least keratinocytes and at least induced or noninduced precursors of Langerhans' cells, at least keratinocytes and at least induced or noninduced precursors of Langerhans' cells are co-cultivated together on the support.

The keratinocytes used according to the invention may be prepared according to any known prior art method. There may be mentioned, by way of example, the culture from a dissociated epidermis derived from a sample of normal or pathological skin or the culture of keratinocytes obtained from the sheath of normal or pathological hair follicles.

Preferably, according to the invention, the keratinocytes used are prepared from a dissociated epidermis derived from a sample of normal or pathological skin, according to the method described in Régnier et al., Frontier of Matrix Biology, Vol. 9, 4–35 (Karger, Basel 1981).

The precursors of Langerhans' cells may be any stem cell capable of undergoing differentiation, under the effect of an induction, into Langerhans' cells, that is to say capable of undergoing differentiation into CD1a-positive cells. Advantageously, these precursors may be $CD34^+$ haematopoietic cells (Caux et al., Nature, Vol. 360, November 1992, 258).

The precursors of Langerhans' cells may be purified from tissues in which they occur naturally, among which there may be mentioned the bone marrow, the peripheral blood, the umbilical cord blood.

Preferably, precursors of Langerhans' cells prepared from peripheral blood or from umbilical cord blood and still more preferably precursors prepared from umbilical cord blood are used according to the process of the invention.

Any purification method can be used for this purpose. There may be mentioned, for example, that described in Caux et al., Nature, Vol. 360, November 1992, 258.

According to the invention, the induction of the differentiation of the precursors of Langerhans' cells may be performed before or after placing them in co-culture.

This induction can obviously be performed by any known method. Among these methods there may be mentioned, for example, the differentiation induced by the cytokines such as colony stimulating factor (Granulocyte/Macrophage-Colony Stimulating Factor or GM-CSF), tumour necrosis factor (TNF-α), Stem Cell Factor (SCF), interleukin-3 or interleukin-4 or a mixture thereof.

However, the applicant has discovered, quite surprisingly, that the differentiation of the precursors of Langerhans' cells can be spontaneously induced by the presence of keratinocytes or alternatively by a culture of these precursors in a medium in which keratinocytes have been previously cultivated.

The induction, in the presence of keratinocytes, can therefore be performed either by a simultaneous culture of precursors of Langerhans' cells and of keratinocytes, the induction taking place in the culture, or by co-culture of the precursors of Langerhans' cells and of keratinocytes on a support, for example, an epidermis-free dermis, the induction taking place within the co-culture.

Preferably, according to the invention, the induction of the differentiation of the precursors of Langerhans' cells is performed by the presence of keratinocytes and still more preferably by co-culture of the precursors of Langerhans' cells and of keratinocytes on a support.

Advantageously, the induction of the differentiation of the precursors of Langerhans' cells can be carried out by the combination of at least two of these methods, such as for example the culture, in the presence of keratinocytes and in the presence of at least one cytokine or alternatively the culture in the presence of a mixture of cytokines, such as for example the combination of GM-CSF and of TNF-α.

The cytokine concentration used for the induction obviously depends on the nature of the cytokine used.

The cytokines are in general present at concentrations of between 1 ng/ml and 400 ng/ml, preferably between 2.5 ng/ml and 300 ng/ml. Thus, for example, for GM-CSF, the concentration may be between 100 ng/ml and 400 ng/ml and preferably between 200 ng/ml and 300 ng/ml. For TNF-α, the concentration may be between 1 ng/ml and 7.5 ng/ml and preferably between 2.5 ng/ml and 5 ng/ml.

Insofar as a mixture of cytokines is used, the proportion of one cytokine relative to another varies according to the nature of the cytokines used. For example, in the case of the GM-CSF/TNF-α mixture, the proportion is between the weight ratios 400/1 and 13/1 and preferably between 120/1 and 40/1.

It is possible for the placing in co-culture to enrich the preparation of induced precursors with CD1a-positive cells. For that, the CD1a-positive cells are isolated from the cultures of induced precursors.

According to the invention, the ratio of the number of keratinocytes to the induced or noninduced precursors of Langerhans' cells, co-cultivated on the support, is between the ratios 95/5 and 25/75 as a percentage of the total number of cells in the co-culture and preferably between 75/25 and 35/65 and still more preferably this ratio is 50/50.

According to the process of the invention, the induced or noninduced precursors of the Langerhans' cells are placed in co-culture at any stage of formation of the epidermis equivalent.

Advantageously, the process according to the invention comprises a step in which the induced or noninduced precursors of the Langerhans' cells are placed in co-culture with the keratinocytes at a time which allows their suprabasal localization in the epidermis equivalent.

Preferably, the induced or noninduced precursors of the Langerhans' cells are placed in co-culture at a time chosen between the moment when the suprabasal layer of the epidermis equivalent begins to form and the moment when the differentiated keratinocytes begin to form the first layer of the stratum corneum.

Still more preferably, the induced or noninduced precursors of Langerhans' cells are placed in co-culture at a time chosen between the moment when the suprabasal layer of the epidermis equivalent begins to form and the second day of incubation after exposure to the air/liquid interface (see below).

The nutrient medium used for the process according to the invention may be any nutrient medium known for its capacity to allow the proliferation and differentiation of the keratinocytes. There may be mentioned, by way of example, the Dulbecco's modified Eagle medium, or a defined medium with a variable calcium content, such as the medium described by Boyce S. T. and Ham R. G., (J. Tissue Cult. Meth., 1985, 9, 83–93).

Advantageously, according to the invention, it is possible to use a mixture of several nutrient media such as, for example, the Dulbecco's modified Eagle medium/HAM F12 medium or Rheinwald and Green medium (Cell, 1975, 6, 331–334).

According to the procedure for preparing the skin equivalent, the co-culture is first maintained immersed in a nutrient medium for an incubation time of 3 to 8 days. This nutrient medium may be, for example, the medium described by Rheinwald and Green, which medium allows the proliferation of the keratinocytes.

At the end of this incubation time, the co-culture is brought to the air/liquid interface, for example by deposition on a metal grid. The liquid then preferably consists of the same nutrient medium as the preceding one, with the difference that only 3 of the growth factors initially contained in the Rheinwald and Green medium are preserved at the same concentrations, namely the epidermal growth factor (EGF), insulin and hydrocortisone.

The incubation is then continued until a skin equivalent is obtained which has the characteristics of a skin, namely a dermis equivalent supporting an epidermis equivalent having the conventional cell layers, namely the basal, suprabasal, granular and corneal layers.

Thus, the incubation is continued for a period of between 5 and 30 days.

The reconstructed skin model thus produced consists of two entities, the support and the epidermis equivalent, which can be physically separated from each other.

The epidermis equivalent can then be used separately from the support.

The invention therefore also relates to an epidermis equivalent, characterized in that it comprises at least keratinocytes and at least induced or noninduced precursors of Langerhans' cells and to the process for preparing it, as described above.

Preferably, the epidermis equivalent according to the invention has at least induced or noninduced precursors of Langerhans' cells located in its suprabasal part.

Of course, the skin equivalent which exhibits the best similarity with normal skin is the skin equivalent which contains the three essential cell types present in normal skin.

Thus, advantageously, the reconstructed skin model according to the invention comprises, in addition, melanocytes.

The invention relates advantageously to an epidermis equivalent containing keratinocytes, at least induced or noninduced precursors of Langerhans' cells and melanocytes.

The melanocytes used according to the invention can be purified from any organ containing them, such as for example normal skin or the hair follicle.

Preferably, melanocytes purified from normal skin are used.

Any purification method known in the prior art can be used to prepare these melanocytes. There may be mentioned, for example, the method described in Olsson et al., Acta Derm. Venereol., 1994, 74, 226–268.

To obtain a skin equivalent containing the three cell types present in normal skin, it is necessary to co-cultivate keratinocytes, induced or noninduced precursors of Langerhans' cells and melanocytes on a support.

Thus, according to another specific mode of the process of the invention, it is characterized in that keratinocytes, at least induced or noninduced precursors of Langerhans' cells and melanocytes are co-cultivated on a support.

In the case of a skin equivalent comprising the three cell types, the process used for its production does not differ in any way from that presented above for the production of a skin equivalent comprising two cell types.

For example, the ratio of the mixture (keratinocytes+ melanocytes) to the Langerhans' cells and/or the precursors co-cultivated on the support is between the ratios 95/5 and 25/75 as a percentage of the total number of cells in the co-culture and preferably between 75/25 and 35/65 and still more preferably this ratio is 50/50.

The specific ratio between keratinocytes and melanocytes may be that described in the prior art (WO-A-9351165).

The examples below illustrate the invention without limiting it in any way.

Example of preparation of an epidermis equivalent containing keratinocytes, Langerhans' cells and melanocytes:

A mixture of normal human keratinocytes previously isolated according to the method described by Régnier et al., (Frontier of Matrix Biology, Vol. 9, 4–35, Karger, Basel 1981) and of human melanocytes previously isolated according to the method described in Olsson et al., (Acta Derm. Venereol., 1994, 74, 226–268) is prepared in a proportion of 10 to 1. This mixture is deposited on an epidermis-free dermis in an amount of $5\times10^5$ cells per cm$^2$, according to the method described by Prunieras et al., Ann. Chir. Plast., 1979, 24, No. 4, 357–362. The culture is carried out in a medium consisting of a Dulbecco's modified Eagle medium and HAM F12 medium in a proportion of 3 to 1, containing 10% foetal calf serum, 10 ng/ml of epidermal growth factor (EGF), 400 ng/ml of hydrocortisone, $10^{-6}$M isoproterenol, 5 µg/ml of transferrin, $2\times10^{-9}$M triiodothyronine, $1.8\times10^{-4}$M adenine and 5 µg/ml of insulin (Rheinwald and Green, Cell, 1975, 6, 331–334). The culture is thus maintained immersed for 6 days. The culture is then placed at the air/liquid interface, the said liquid then consisting of the same medium as above from which the isoproterenol, transferrin, triiodothyronine and adenine have been removed.

In parallel, CD34$^+$ cells are isolated from umbilical cord blood and cultivated according to the method described in Caux et al., (Nature, Vol. 360, 19 Nov. 1992, pp. 258–260), for 6 days in the presence of colony stimulating factor (granulocyte/macrophage—colony stimulating factor or GM-CSF) at the concentration of 200 ng/ml and of tumour necrosis factor (TNF-α) at the concentration of 2.5 ng/ml. 2 days after passage of the keratinocyte/melanocyte mixture at the air/liquid interface, $5\times10^5$ CD34$^+$ cells as prepared beforehand are deposited on the epidermis being reconstructed. The culture is then maintained until a histologically satisfactory epidermis equivalent is obtained, that is to say an epidermis equivalent having the conventional cell layers, namely the basal, suprabasal, granular and corneal layers.

Preparation of an epidermis equivalent containing keratinocytes and Langerhans' cells, without preinduction of the precursors of Langerhans' cells:

A mixture of normal human keratinocytes previously isolated according to the method described by Régnier et al., (Frontier of Matrix Biology, Vol. 9, 4–35, Karger, Basel 1981) and of CD34$^+$ cells isolated from umbilical cord blood according to the method described in Caux et al., (Nature, Vol. 360, 19 Nov. 1992, pp. 258–260) is prepared in a proportion of 1 to 1. This mixture is deposited on an epidermis-free dermis in an amount of $5\times10^5$ cells of each type per cm$^2$, according to the method described in Prunieras et al., (Ann. Chir. Plast., 1979, 24, No. 4, 357–362). The co-culture is performed in a medium consisting of a mixture of Dulbecco's modified Eagle medium, HAM F12 in a volume ratio of 3 to 1, containing 10% foetal calf serum, 10 ng/ml of epidermal growth factor (EGF), 400 ng/ml of hydrocortisone, $10^{-6}$M isoproterenol, 5 μg/ml of transferrin, $2\times10^{-9}$M triiodothyronine, $1.8\times10^4$M adenine and 5 μg/ml of insulin (Rheinwald and Green, Cell, 1975, 6, 331–334). The culture is thus maintained immersed for 6 days. The culture is then placed at the air/liquid interface, the said liquid then consisting of the same medium as above from which the isoproterenol, transferrin, triiodothyronine and adenine have been removed.

The co-culture is then maintained until a histologically satisfactory epidermis equivalent is obtained, that is to say an epidermis equivalent having conventional cell layers, namely the basal, suprabasal, granular and corneal layers.

What is claimed is:

1. Skin equivalent which comprises an epidermis equivalent on a support, said epidermis equivalent comprising keratinocytes and induced or noninduced precursors of Langerhans' cells wherein the ratio of the number of keratinocytes to the induced or noninduced precursors of Langerhans' cells ranges from 95/5 to 25/75 based on the percentage of the total number of cells in the epidermis equivalent.

2. Skin equivalent according to claim 1, wherein the support is selected from the group consisting of mixed collagen/fibroblast lattices, dermis previously freed of the epidermis, artificial membranes, collagen-based subcutaneous substitutes, and plastic or any other support materials which maintain cell viability.

3. Skin equivalent according to claim 2, wherein the support consists of dermis previously freed of the epidermis.

4. Skin equivalent according to claim 1, which further comprises melanocytes.

5. Skin equivalent according to claim 1, wherein the induced or noninduced precursors of Langerhans' cells are suprabasally localized in the epidermis equivalent.

6. Process for preparing a skin equivalent, which comprises co-cultivating keratinocytes and at least induced or noninduced precursors of Langerhans' cells on a support.

7. Process according to claim 6, wherein the ratio of the number of keratinocytes to the induced or noninduced precursors of Langerhans' cells, co-cultivated on the support, ranges from 95/5 to 25/75 based on the percentage of the total number of cells in the co-culture.

8. Process according to claim 6, wherein the keratinocytes are obtained by culturing a dissociated epidermis derived from a sample of normal or pathological skin or by culturing keratinocytes obtained from the sheath of normal or pathological hair follicles.

9. Process according to claim 8, wherein the keratinocytes are obtained from a sample of normal or pathological skin.

10. Process according to claim 6, wherein the precursors of the Langerhans' cells are purified from bone marrow, peripheral blood or umbilical cord blood.

11. Process according to claim 10, wherein the precursors of the Langerhans' cells are purified from umbilical cord blood.

12. Process according to claim 6, wherein the precursors of Langerhans' cells are CD34$^+$ haematopoietic cells.

13. Process according to claim 6, wherein the precursors of Langerhans' cells are induced before or after placing them in co-culture.

14. Process according to claim 13, wherein the precursors of Langerhans' cells are induced after placing them in co-culture.

15. Process according to claim 13, wherein the precursors of Langerhans' cells are induced according to a method selected from the group consisting of culturing in the presence of keratinocytes, culturing in a medium in which keratinocytes have been previously cultivated, and culturing in the presence of a cytokine selected from the group consisting of colony stimulating factor, tumor necrosis factor, stem cell factor, interleukin-3 and interleukin-4.

16. Process according to claim 15, wherein said precursors are induced by the combination of at least two of the methods selected from the group consisting of culturing in the presence of keratinocytes, culturing in a medium in which keratinocytes have been previously cultivated, culturing in the presence of a cytokine selected from the group consisting of colony-stimulating factor, tumor necrosis factor, stem cell factor, interleukin-3 and interleukin-4.

17. Process according to claim 16, wherein said precursors are induced by culturing in the presence of keratinocytes and in the presence of at least one cytokine or by culturing in the presence of a mixture of cytokines.

18. Process according to claim 17, wherein said precursors are induced by culturing in a medium containing GM-CSF and TNF-α.

19. Process according to claim 6, wherein co-cultivating is effected in a medium containing cytokines which are present at concentrations ranging from 1 ng/ml to 400 ng/ml.

20. Process according to claim 19, wherein the medium contains GM-CSF present at a concentration ranging from 100 ng/ml to 400 ng/ml.

21. Process according to claim 6, wherein co-cultivating is effected in a medium containing TNF-α at a concentration ranging from 1 ng/ml to 7.5 ng/ml.

22. Process according to claim 18, wherein the GM-CSF/TNF-α proportion ranges from a weight ratio of 400/1 to 13/1.

23. Process according to claim 6, wherein the induced or noninduced precursors of the Langerhans' cells are placed in a co-culture containing keratinocytes at a time which allows for them to become localized in the suprabasal part of the epidermis equivalent.

24. Process according to claim 23, wherein the induced or noninduced precursors of the Langerhans' cells are placed in culture at a time selected from the group consisting of about the time when the suprabasal layer of the epidermis equivalent begins to form and about the time when the differentiated keratinocytes begin to form the first layer of the stratum corneum.

25. Process according to claim 24, wherein the induced or noninduced precursors of the Langerhans' cells are placed in co-culture at a time selected from the group consisting of about the time when the suprabasal layer of the epidermis equivalent begins to form and the second day of culture after passage to the air/liquid interface.

26. Process according to claim 6, wherein said co-cultivation occurs in the presence of melanocytes.

27. Epidermis equivalent, which comprises keratinocytes and induced or noninduced precursors of the Langerhans' cells.

28. Epidermis equivalent according to claim 27, which further comprises melanocytes.

29. Epidermis equivalent according to claim 27, wherein the induced or noninduced precursors of the Langerhans' cells are suprabasally localized.

30. The skin equivalent of claim 2, wherein the artificial membrane is a Millipore filter membrane material.

31. The process according to claim 7, wherein the ratio of keratinocytes to induced or non-induced precursors of Langerhans' cells ranges from 75/25 to 35/65 based on the percentage of the total number of cells in the co-culture.

32. The process according to claim 7, wherein the ratio of keratinocytes to Langerhans' cells ranges is about 50/50 based on the percentage of the total number of cells in the co-culture.

33. The process according to claim 19, wherein the cytokine concentration ranges from 2.5 ng/ml to 300 ng/ml.

34. The process according to claim 20, wherein the GM-CSF concentration ranges from 200 ng/ml to 300 ng/ml.

35. The process according to claim 21, wherein the TNF-α concentration ranges from 2.5 ng/ml to 5 ng/ml.

36. The process according to claim 22, wherein the GM-CSF/TNF-α cytokine concentration weight ratio ranges from 120/1 to 40/1.

* * * * *